(12) United States Patent
Adrian (10) Patent No.: US 6,203,537 B1
(45) Date of Patent: Mar. 20, 2001

(54) LASER-DRIVEN ACOUSTIC ABLATION CATHETER

(76) Inventor: Sorin Adrian, 311 Fawn Hill La., Penn Valley, PA (US) 19072

( * ) Notice: Subject to any disclaimer, the term of this patent is extended or adjusted under 35 U.S.C. 154(b) by 0 days.

(21) Appl. No.: 09/244,850

(22) Filed: Feb. 4, 1999

(51) Int. Cl.[7] .................................................... A61B 17/00
(52) U.S. Cl. .................................. 606/1; 606/128; 601/4; 604/22; 604/35
(58) Field of Search ............................... 606/3, 7, 13, 15, 606/17, 128, 171, 2.5, 1; 604/20, 21, 35, 523, 22; 601/4; 600/439

(56) References Cited

U.S. PATENT DOCUMENTS

| | | |
|---|---|---|
| 5,224,942 | * 7/1993 | Beuchat et al. ........................ 606/15 |
| 5,246,447 | * 9/1993 | Rosen et al. ........................... 606/128 |

* cited by examiner

*Primary Examiner*—Lee Cohen
(74) *Attorney, Agent, or Firm*—William H. Meise (57) ABSTRACT

An acoustic ablation catheter includes a mass cap mounted by a spring at the distal end of the catheter, to thereby form a structure capable of axial motion with a resonant frequency. The mass cap defines an aperture which may be used for a guide wire, for aspiration/infusion, or both. Acoustic motion of the resonant structure is generated by sources of laser light spaced about the distal end of the flexible portion of the catheter body, which produce laser light beams which produce microexplosions adjacent the proximal end of the mass cap. The sources of laser light beams may be laser chips located at the distal end of the body, or they may be the distal ends of optical fibers extending through the body from laser light generators outside the catheter itself. In one advantageous embodiment, relative motion is introduced between the mass cap and the light beams, so that erosion is distributed over a track. At least that portion of the mass cap upon which the laser light pulses impinge is made from titanium.

22 Claims, 5 Drawing Sheets

LASER-DRIVEN ACOUSTIC ABLATION CATHETER

FIELD OF THE INVENTION

This invention relates to medical devices generally, and more particularly to ablation catheters.

BACKGROUND OF THE INVENTION

Angioplasty catheters are widely used for removing plaque from arteries. Some "roto-rooter" angioplasty catheters have rotary blades, which cut away the excess plaque. These catheters may cause damage to the coronary arteries.

An impact lithotripsy catheter is described in U.S. Pat. No. 5,246,447, issued Sep. 21, 1993 in the name of Rosen et al. This catheter includes a mass cap, supported by the windings of helically wound guide, at the distal end of the catheter. Laser pulses are applied through an optical fiber extending axially through the body of the catheter, to vaporize a portion of the mass cap at each pulse. The vaporization, in turn, results in rapid expansion of material at the proximal end of the mass cap, which generates a high velocity, short forward impulse. The impulse is transmitted through the mass cap to the kidney stone or other hard deposit. While effective in fragmenting calciferous and other hard deposits, this type of catheter may not remove soft or fatty deposits.

Acoustic catheters are used for angioplasty, for ablating plaque by sonification of the fluid in the affected artery. Some acoustic ablative catheters have a metal wire extending through the body of the catheter, and have an acoustic generator external to the body, and coupled to the proximal end of the metal wire. These catheters suffer from the problem of standing waves along the length of the wire, and of heating at nodes of the standing wave pattern. This type of acoustic ablation catheter has relatively low efficiency in coupling energy from the acoustic generator to the ablation site, because of heating losses at the nodes of the standing wave. Consequently, it is necessary to apply considerable acoustic power to the proximal end of the catheter, in order to couple enough energy to the catheter to effectively ablate plaque at the proximal end in the presence of the losses. The heating losses at the nodes, with this large acoustic input power, may cause damage to the patient at the locations of the nodes.

U.S. Pat. No. 5,423,797, issued Jun. 13, 1995 in the name of Adrian et al. describes an ablation catheter which includes a rotary-to-axial motion converter at its distal end, driven by a rotating shaft. The motion converter converts the rotary motion of the shaft into axially-directed acoustic pulsations, which are coupled to the surrounding fluid to thereby generate the acoustic energy by which ablation is accomplished. In one embodiment described therein, the motion converter includes an uneven or wavy surface (swash plate) which is rotated by the shaft, and a follower which is free for axial motion, which bears against the wavy surface, and is pushed distally by the protruding portions of the surface. While effective at generating acoustic energy, this type of catheter involves the use of moving parts.

Improved acoustic catheters are desired.

SUMMARY OF THE INVENTION

An ablation catheter according to the invention includes an elongated, flexible body defining a distal end, a proximal end, and a local axis, and a mass cap defining a proximal portion and a distal portion. A resilient mounting arrangement includes a proximal end and a distal end. The proximal end of the resilient mounting arrangement is physically coupled to the distal end of the body of the catheter, and the distal end of the resilient mounting arrangement is physically coupled to the mass cap, for holding the mass cap adjacent to the distal end of the catheter body. The resilient mounting arrangement defines either (one of) (a) transparent and (b) open regions, with the transparent or open regions lying between the distal end of the catheter body and the mass cap. The ablation catheter also includes at least one laser light radiator or source for producing one or more light beam(s). The laser light source is located near the distal end of the catheter body, and is oriented so as to project its light beam parallel to the local axis, through an open or transparent portion of the resilient mounting arrangement, to a proximal portion of the mass cap. In a particularly advantageous embodiment of the invention, the laser beam is focussed on a surface of the mass cap.

In a particularly advantageous embodiment of the invention, the ablation catheter is part of an ablation catheter system in which the mass cap, in conjunction with the resilient mounting arrangement, makes a physically resonant system defining a fundamental resonant frequency. In this catheter system, a laser light source driving arrangement external to the catheter drives the laser light source in such a manner as to generate the laser light in pulses having a repetition rate which is near the fundamental frequency of the oscillatory mechanical system formed by the cap/spring arrangement, or a multiple (sometimes known as a harmonic) of this repetition rate, and for, together with the ablation catheter, forming an ablation catheter system.

In another embodiment of the catheter according to the invention, which may be used in the ablation catheter system, the laser light source(s) comprise semiconductor laser chips, and further comprise an electrical conducting arrangement extending from the semiconductor laser chip(s) to the proximal end of the catheter. Each of the laser light sources may include a laser located outside the body of the catheter, a source of electrical energy coupled to the laser by arrangement lying outside of the catheter body, and an optical fiber light path extending from the laser, through the proximal end of the catheter, through the body of the catheter, and to the distal end of the catheter.

In a particularly advantageous embodiment of the invention, the mass cap further defines an aperture, the body of the catheter defines a lumen extending from a region near the proximal end of the catheter body to the distal end of the catheter body, and the resilient mounting arrangement also defines a path extending from the aperture of the mass cap to the distal end of the lumen of the catheter body. The aperture of the mass cap, the path of the resilient mounting arrangement, and that portion of the lumen of the catheter body near the distal end of the catheter body may be radially centered between the laser light sources. The mass cap and the body of the catheter may further define aspiration/infusion apertures, coupled together for the flow of fluid therebetween and together extending from a region near the proximal end of the catheter body to the distal end of the mass cap.

A more particular embodiment of the ablation catheter according to the invention includes an elongated, flexible body defining a distal end, a proximal end, and a local axis, and a mass cap defining a proximal portion and a distal portion. A resilient mounting arrangement including a proximal end and a distal end. The proximal end of the resilient mounting arrangement is physically coupled to the distal end of the body of the catheter, and the distal end of the resilient mounting arrangement is physically coupled to the mass cap, for holding the mass cap adjacent to the distal end of the catheter body. The resilient mounting arrangement defines at least one of a transparent region and an open region lying between the distal end of the catheter body and the mass cap. A plurality of laser light sources is provided, each of which produces a light beam. Each of the laser light sources is physically coupled to the distal end of the catheter body. Each of the plurality of laser light sources is circumferentially located relative to the local axis, and equally spaced about the local axis relative to others of the laser light sources, and oriented so as to project its light beam parallel to the local axis, through an optically transparent region (including an open region) of the resilient mounting arrangement, to a proximal portion of the mass cap. In a particularly advantageous version of this embodiment, the mass cap in conjunction with the resilient mounting arrangement makes a physically resonant system defining a fundamental resonant frequency, and also includes a laser light source driving arrangement. The laser light source driving arrangement includes an arrangement for driving the laser light sources, so as to generate the laser light in pulses having a repetition rate which includes components near one of (or either of) (a) the fundamental frequency and (b) multiples of the repetition rate. Put another way, the repetition rate of the light pulses is selected to be near the frequency of mechanical resonance of the mass-cap/spring arrangement, or at a multiple of that repetition rate. The laser light source driving arrangement also, together with the ablation catheter, forms an ablation catheter system. The laser light sources at the distal end of the catheter body may include semiconductor laser chips, and may further include an electrical conducting arrangement extending from the semiconductor laser chips to the proximal end of the catheter. In another embodiment, each of the laser light sources may include a laser located outside the body of the catheter, and an optical fiber light path extending from the external laser, through the proximal end of the catheter, through the body of the catheter, and to the distal end of the catheter, and more particularly to the proximal end of the mass cap. In order to accommodate a guide wire, or for aspiration or infusion (aspiration/infusion), the mass cap may further define an aperture, the body of the catheter may define a lumen extending from a region near the proximal end of the catheter body to the distal end of the catheter body, and the resilient mounting arrangement may also define a path extending from the aperture of the mass cap to the distal end of the lumen of the catheter body, and these paths may be centered in the surrounding structure, if desired. If such a combination of lumens, open spaces, and apertures is provided for use with a guide wire, the mass cap of the catheter may also include a further aspiration/infusion aperture, and the body of the catheter may define a further aspiration/infusion lumen extending from a region near the proximal end of the catheter body to the distal end of the catheter body. In this last embodiment, the opening of the resilient arrangement may be used by both the guide wire and by the aspiration/infusion path.

DESCRIPTION OF THE INVENTION

In FIGS. 1, 2*a*, 2*b*, and 2*c*, an ablation catheter system 10 includes an ablation catheter 11, which includes an elongated, flexible body 12 defining a distal end 14, a proximal end 16, and a local axis 8 at each location along the flexible body. Catheter 11 also includes a "mass cap" 18 defining a distal portion 18*d*, and also defining a proximal portion 18*p*. A resilient mounting arrangement in the form of a helical spring 20 includes a proximal end 20*p* and a distal end 20*d*, as is more readily seen in FIG. 2*c*. The proximal end 20*p* of the resilient mounting arrangement 20 is physically coupled to the distal end 14 of the body 12 of the catheter, and the distal end 20*d* of the resilient mounting arrangement 20 is physically coupled to the proximal end 18*p* of mass cap 18, for holding the mass cap 18 in its location adjacent to the distal end 14 of the catheter body 12.

Figure 1:
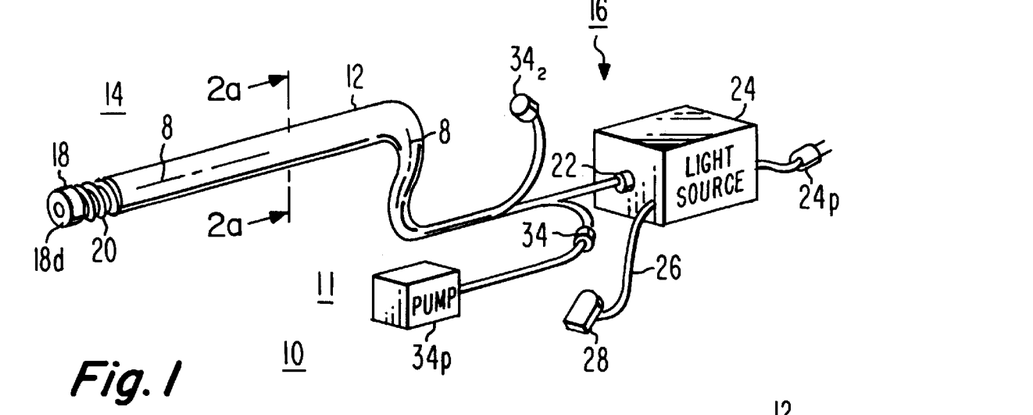
FIG. 1 is simplified perspective or isometric view of an acoustic ablation catheter according to an aspect of the invention

As illustrated in FIG. 1, the proximal end 16 of flexible body 12 of catheter 11 is connected by way of a connection arrangement, illustrated as a connector 22, with a source of laser light, illustrated as a box 24. The ON and OFF state of the laser light is controlled, as for example by a foot-operated switch 28 connected to box 24 by a set 26 of wires. Power for box 24 is provided by an electrical cord and plug 24*p*.

Figure 2A:
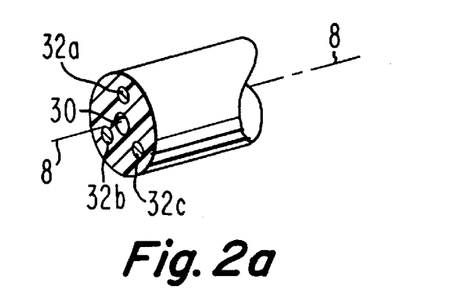
FIG. 2*a* is a simplified perspective or isometric cross-section of the catheter of FIG. 1 at a location along its length.
Figure 2B:
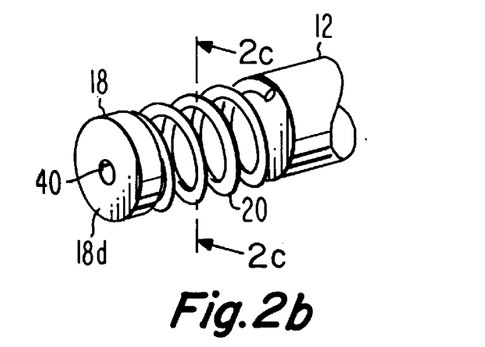
FIG. 2*b* is a corresponding view of the distal end of the catheter body, the resilient spring, and the mass cap.

In FIG. 2*a*, the flexible body 12 has a central aspiration or infusion channel 30, and three optical fibers 32*a*, 32*b*, and 32c extending parallel to local axis 8, for carrying light pulses from the proximal end 16 of the catheter body 12 to the distal end 14. Aspiration or infusion channel 30 terminates at the proximal end of the body in a suitable connector 34, as illustrated in FIG. 1, which may be connected to an infusion or medication pump illustrated as a block 34p. In FIG. 2b, the mass cap 18 defines a through aperture 40. A further aspiration channel (not illustrated) may be provided, which connects to a second connector designated $34_2$.

Figure 2C:
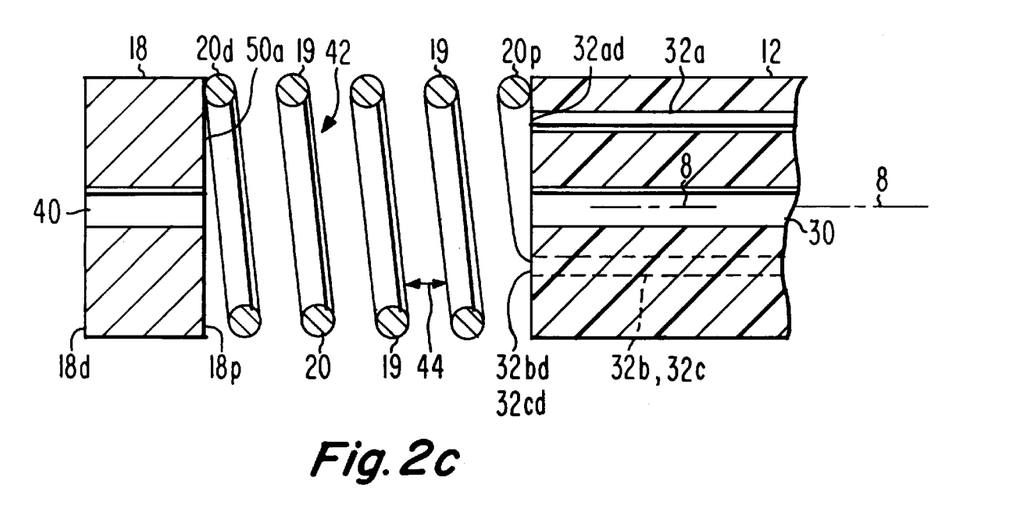
FIG. 2*c* is a simplified cross-section of the distal end of catheter body, the mass cap, and the resilient spring.

In FIG. 2c, the resilient spring is in the form of multiple turns of a single spring wire of circular cross-section, each turn of which, in cross-section, appears as a separate piece or segment. Some of pieces or segments of the spring 18 are designated as 19. FIG. 2c shows that mass cap 18 is supported at its proximal end 18p by the distal end 20d of the resilient spring 20, and spring 20 is supported at its proximal end 20p by being affixed to the distal end of the catheter body 12. Further, aspiration/infusion lumen 30 of the catheter body 12 is coaxial with the aspiration/infusion aperture 40 in the mass cap. The presence of an aspiration/infusion aperture in the mass cap avoids the need for reliance on perfusion through the spaced-apart turns of the coil of the spring, which will often be in intimate contact with the walls of a vas or blood vessel in which the catheter is used. Thus, the aperture 40 in mass cap 18, together with the open region 42 defined by the helical windings of spring 20, allows easy flow of fluids to and from aspiration/infusion lumen 30, regardless of the spacing, illustrated as 44, between adjacent windings 19 of spring 20, and also regardless of the presence or absence of flesh or the walls of a vas in obturating or sealing the spaces 44 between adjacent windings 19.

A laser light source within box 24 of FIG. 1 projects laser light, in the form of pulses, to the distal end of optical fiber 32a of FIG. 2c, so that the laser light leaves the distal end 32ad of the optical fiber, and is focussed, or projected directly, across open region 42, parallel with the local axis 8, to fall onto a location designated 50a on the proximal side or end 18p of mass cap 18. As known to those skilled in the art, the projection of a laser light beam, in pulses, onto the proximal end 18p of a mass cap such as 18, causes microscopic plasma-generated explosions attributable to vaporization of the mass cap itself, vaporization of the fluid adjacent to the mass cap, or both.

It has been discovered that these microscopic explosions, in turn, create compression pulses in the mass cap 18 itself, which compression pulses are carried from the proximal end 18p through the mass cap 18 to cause the distal end 18d of the mass cap 18 to vibrate acoustically at a frequency which is determined principally by the mass of the mass cap and the characteristics of the resilient mounting of the mass cap. The acoustic vibrations of the distal end 18p of the mass cap 18, in turn, cause generation of axially-directed acoustic vibrations in the surrounding fluid medium. An alternative viewpoint is that the microscopic explosions push the mass cap in a distal or forward direction, thereby exciting the mechanical resonant circuit, which thereafter vibrates with a frequency determined by the characteristics of the spring and mass cap (and the characteristics of other elements coupled to the spring and mass cap), and damped or amortized by the characteristics of the medium surrounding the mass cap and spring. The actual acoustic signal generated in the surrounding medium may be attributable to both direct generation of compression waves and excitation of the resonant mass circuit.

Figure 3A:
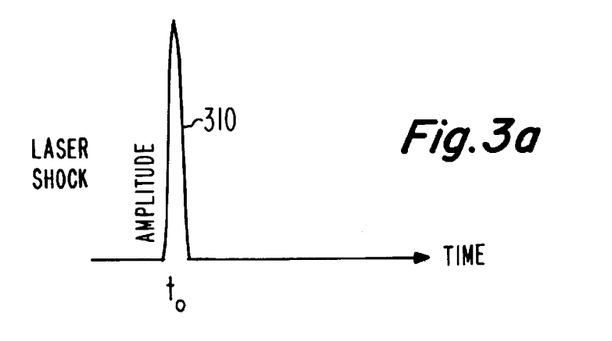
FIG. 3*a* illustrates a plot of laser light amplitude or energy versus time.
Figure 3B:
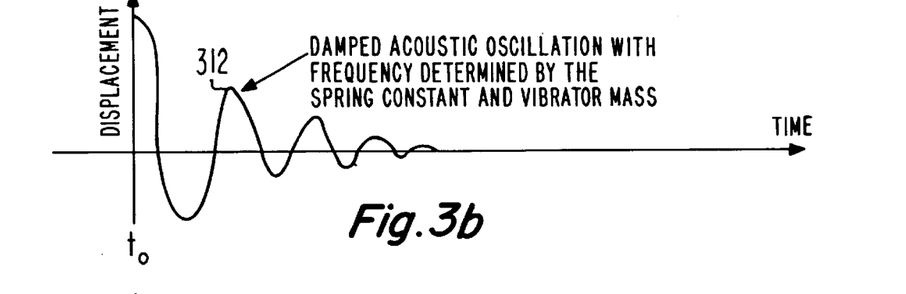
FIG. 3*b* is a plot of displacement of the mass cap of an excited spring/mass cap system versus time.
Figure 3C:
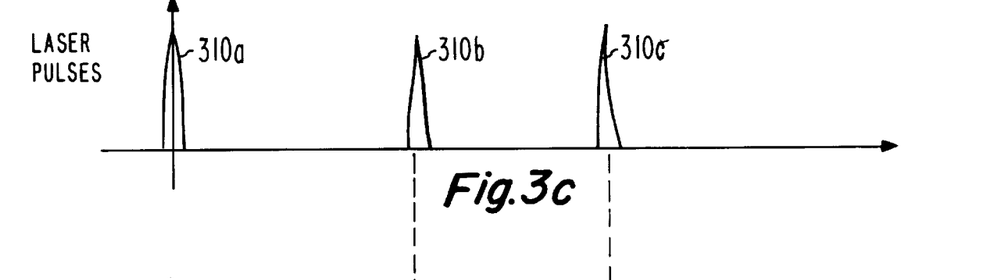
FIG. 3*c* is a plot of a train of laser pulses.
Figure 3D:
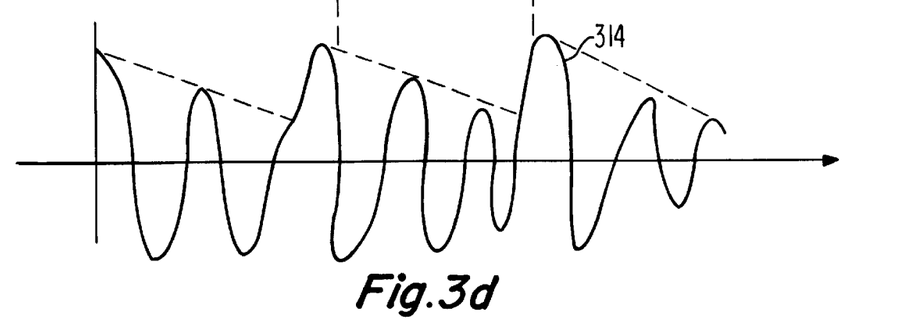
FIG. 3*d* is a plot of recurrent damped displacement of a resonant system excited by in-phase pulses of FIG. 3*c*.

The presence of fluid surrounding the mass cap tends to damp vibration as acoustic energy is transferred from the mass cap to the surrounding fluid medium, but does not significantly affect the resonant frequency. FIG. 3a is a representation of a laser pulse 310 occurring at time $t_0$. FIG. 3b is a plot 312 of axial vibration displacement amplitude versus time for a resonant mass excited by the laser pulse at time $t_0$. As illustrated, the displacement is initially a large positive value, which makes recurrent excursions across the zero axis with a frequency established by the spring constant and the mass, and with displacement amplitude decreasing with increasing time due to damping by the surrounding fluid medium. FIG. 3c represents a train of laser pulses 310a, 310b, 310c, . . . defining a repetition rate 1/t, where t is the pulse-to-pulse interval, which shock-excites the resonant spring/mass cap arrangement 18, 20 at times selected to coincide with a positive peak displacement of the mass cap, as illustrated by plot 314 of FIG. 3d, in order to make up the losses due to conversion of vibratory or acoustic energy into axially-directed acoustic waves, to thereby maintain more-or-less continuous physical resonance. According to an aspect of the invention, the laser light source 24 of FIG. 1 produces the laser pulses 310 at a recurrence rate which is equal to the interval between the damped pulses of FIG. 3d, or at an integer multiple thereof, which corresponds to a frequency equal to the resonant frequency, or a sub-multiple thereof. As a simplified specific example, if the oscillatory mechanical system has a 10 Hz fundamental frequency, corresponding to a 0.1 sec. repetition rate, the laser pulses could have repetition rates of 0.1 sec, 0.2 sec, 0.3 sec., or more generally NX, where N is an integer, and X is the fundamental repetition rate. The repetition rates of 0.2, 0.3 etc. seconds may be termed "submultiples" of the fundamental repetition rate of 0.1 sec.

Figure 4:
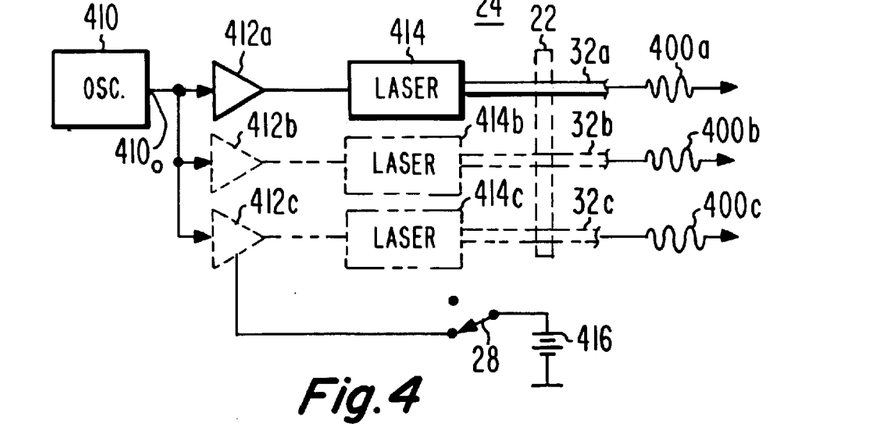
FIG. 4 is a simplified diagram, in block and schematic form, illustrating how the laser pulse train of FIG. 3*c* can be generated.

FIG. 4 is a simplified representation of an arrangement for producing a pulse train having a frequency which corresponds to the resonant frequency of a resonant spring/mass cap. In FIG. 4, a controllable-frequency oscillator 410 produces pulsatory oscillations at an output port 410o, which are applied to an amplifier 412a. Amplifier 412a is energized by a power source illustrated as a battery 416 only during those times in which the foot-pedal switch 28 is depressed. When energized by battery 416, amplifier 412a amplifies the pulsatory oscillations from oscillator 410, to produce amplified electrical pulses for application to laser 414. Laser 414, in turn, responds to the electrical pulses from amplifier 412a to produce pulses of laser light. The frequency of the controllable oscillator 410 is adjusted to correspond to the resonant frequency of the spring/mass cap structure, or to a sub-multiple frequency.

The presence of aperture 30 in mass cap 18 of FIG. 2c does not permit the projection of a laser beam onto the center of the proximal end 18p of the mass cap 18. This, in turn, means that the laser beam which produces the oscillatory excitation can only be applied off-center. Off-center excitation, however, results in acoustic compression waves which progress from the proximal end 18p to the distal end 18d within the mass cap 18 at an angle relative to the local axis 8. This non-axial acoustic wave, in turn, results in an acoustic wave in the surrounding medium which is also off-center.

Figure 5:
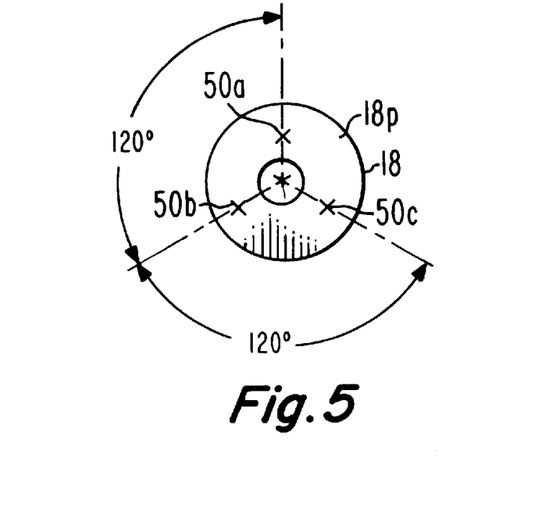
FIG. 5 is a view of the proximal end of the mass cap of FIGS. 2*a*, 2*b*, and 2*c*, showing the locations on which three laser beams impinge.

According to an aspect of the invention, plural laser beams are used to excite the spring/mass cap structure at locations which are spaced about the central aperture 40 of the mass cap. In a preferred embodiment of the invention, the locations on which the laser beams intercept the proximal end 18p of the mass cap 18 are equally spaced about the axis; thus, if two laser beams are used, their impingement locations would be 180° apart, or diametrically located relative to the local axis 8. In the embodiment illustrated in FIGS. 2a, 2b, and 2c, three laser beams are provided by the three optical fibers 32a, 32b, and 32c, and FIG. 5 illustrates that the locations 50a, 50b, and 50c at which the laser beams impinge on the proximal side 18p of mass cap 18 are angularly spaced at 120° about the local axis 8. The symmetrical locations of the laser beam impingements on the mass cap result in simultaneous stimulation or excitation of the resonant spring/mass-cap arrangement 18,20, with the result that the resulting acoustic wave is axially directed. For simultaneous energization of three lasers within laser source 24 of FIG. 1, block 24 may include further amplifiers and lasers, as suggested by phantom amplifiers 412b and 412c, and phantom lasers 414b and 414c in FIG. 4, which are simultaneously energized by switch 28.

Figure 6:
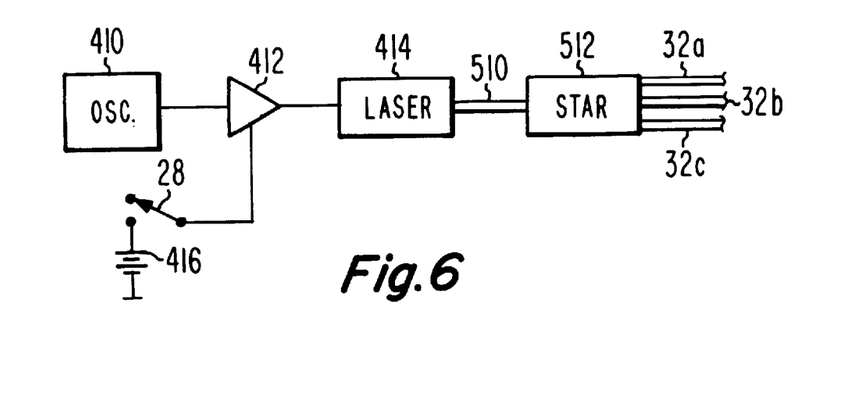
FIG. 6 is a simplified diagram in block and schematic form which illustrates an arrangement for generating plural light beams from a single laser.

FIG. 6 illustrates another way in which the three laser beams of FIG. 5 can be generated in the laser source 24 of FIG. 1. In FIG. 5, the oscillator 410 and amplifier 412 are similar to those of FIG. 4, and amplifier 410 is similarly energized by foot-switch 28. The electrical pulses are applied to a laser 414 as in FIG. 4, but the laser light, instead of being applied directly to optical fiber 32a, is instead applied through a path 510 and a light splitter 512. Light splitter 512 is preferably an optical star, such as those made by fusing multiple optical fibers at one location, but any splitting technique can be used. Light splitter 512 divides the light pulses from laser 414 into multiple portions, at least some of which are coupled to optical fiber paths 32a, 32b, and 32c, which carry the pulses to the distal end of the catheter body 12, and project them onto the proximal end 18p of the mass cap 18.

Figure 7:
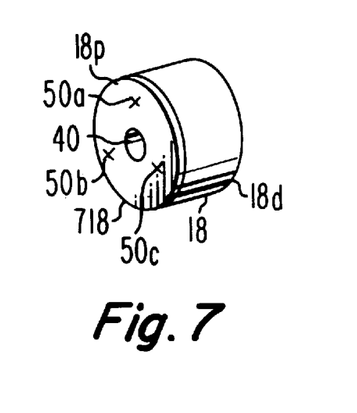
FIG. 7 is a simplified perspective or isometric view of a mass cap usable in the invention, which is made from two different materials.

The optically driven, plasma-generated microexplosion occurring when light hits the mass cap or target is thought to arise from vaporization of the target itself and of the fluid or blood in the vicinity of the proximal end 18p of the mass cap 18. It is believed that the laser pulse striking the target dislodges electrons which generate a plasma in the vicinity of the target. The target material must therefore have characteristics of (a) low chemical activity at high temperatures to prevent oxidation and the like, (b) low-to-average electron activation energy, and (c) relatively low thermal conductivity, so that the energy of the laser pulse is not readily conducted away from the laser impingement point, which would reduce the plasma generation at the impingement site. According to a further aspect of the invention, at least the proximal end of the mass cap, onto which the laser beam or beams are projected, is made from titanium, which is relatively inert in the presence of water and biological materials, has an average activation energy, and one of the lowest heat conductivities among noble metals. The use of titanium, instead of iron, for example, prevents degradation and erosion of the mass cap at the laser pulse impingement site. Such erosion could occur very rapidly if iron were used, because the high temperatures at the point of impingement would enhance oxidation and carbonization, as a result of which a pit or valley would be formed in the mass cap, which would change its mass, and thereby change its resonant frequency away from the proper relationship with the pulse frequency. In FIG. 7, the proximal end 18p of mass cap 18 is visible. The main body of the mass cap is made from magnesium or aluminum, for strength with low mass, to thereby tend to maximize the resonant frequency of the spring/mass cap combination. The proximal end of the mass cap is coated with a thin layer of titanium designated as 718.

Figure 8:
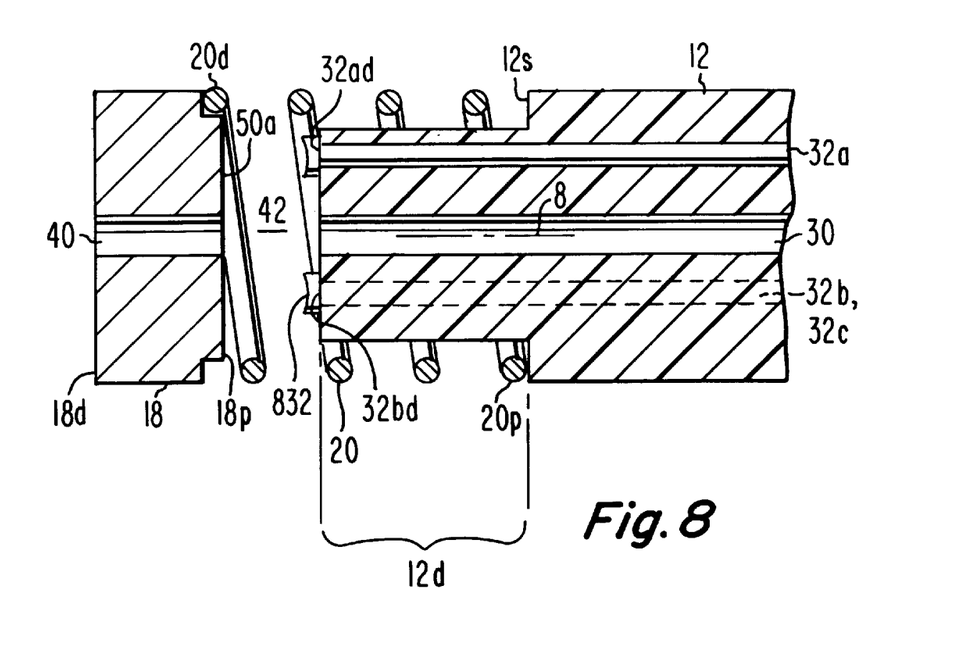
FIG. 8 is a simplified cross-section of the distal end of an acoustic ablation catheter according to another aspect of the invention.

FIG. 8 is similar to FIG. 2c, but illustrates how the distal end 32ad of the optical fiber 32a can be brought closer to the mass cap, without affecting the axial length of spring 20, and therefore without affecting the resonant frequency of the spring/mass-cap structure. As illustrated in FIG. 8, the most proximal turn 20p of spring 20 abuts a shoulder 12s, to which the spring is affixed, as by adhesive. That portion of body 12 which is more distal than shoulder 12s is designated 12d, and has a diameter smaller than the diameter of open region 42 defined within the turns of coil 20, so that the spring does not rub or bear against the body portion 12d. This leaves spring 20 free to compress and expand axially, just as in the arrangement of FIG. 2c. The arrangement of FIG. 8 has the advantage over that of FIG. 2c that the laser pulses have a lesser distance to travel between the end of the guiding optical fiber (such as 32a) before impinging on the target point 50, and this tends to reduce losses in the light pulse which would otherwise cause laser pulse energy to be expended in vaporizing any opaque or optically lossy material, such as blood cells, in the intervening path. Vaporization of matter far from the proximal surface of mass cap 18 does not contribute to generation of acoustic waves by resonance of the spring/mass-cap structure.

As also illustrated in FIG. 8, a lens arrangement illustrated as 832 may be affixed to, or formed, cut or defined in, the distal end of each of the optical fibers, such as fiber 32a, to tend to focus the laser beam onto the surface of the target.

Figure 9A:
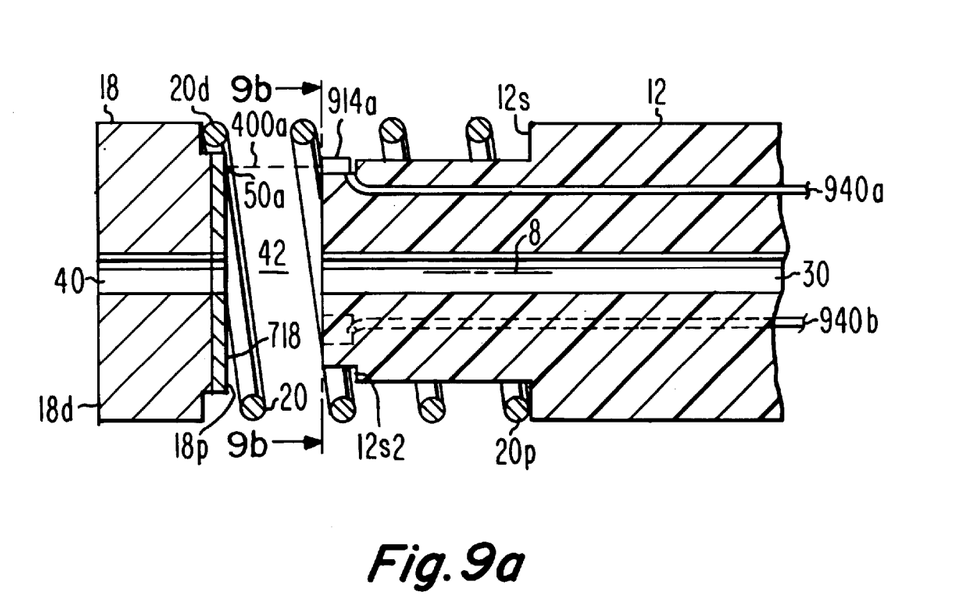
FIG. 9*a* is a simplified cross-section of the distal end of an acoustic ablation catheter according to an aspect of the invention, in which the laser chips are physically located near the distal end of the catheter.
Figure 9B:
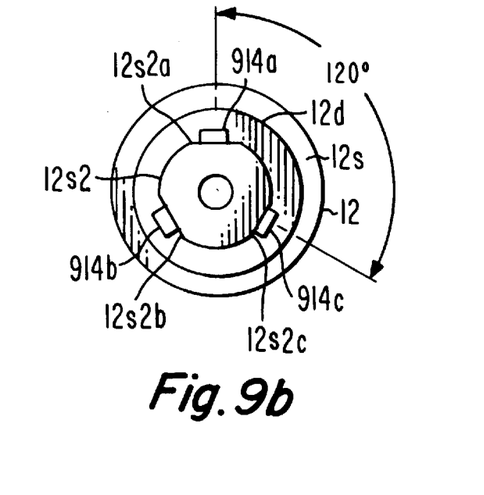
FIG. 9*b* is an end view thereof taken looking in the direction of section lines 9*b*–9*b*.
Figure 10:
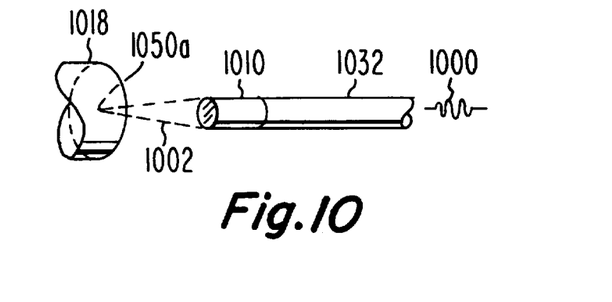
FIG. 10 is a simplified representation of an optical fiber 1032 which may be used in a catheter according to the invention, together with a focussing device.

In FIGS. 9a and 9b, the light sources, instead of being in the form of optical fibers terminating near the distal end of the catheter and driven by light pulses from outside the catheter, are in the form of laser chips which are physically located near the distal end of the catheter, and which project their light beams directly onto the mass cap without intermediary optical fibers, although lenses may be useful in such an arrangement, and lenses may take the form of short segments of appropriately graded optical fiber, as known in the art, and as described in conjunction with FIG. 10. In FIGS. 9a and 9b, the distal end of catheter body portion 12d defines a further step 12s2, at least in the region at which the laser chips are to be placed, to form flats 12s2a, 12s2b, and 12s2c. The laser chips, appropriately protected by encapsulation or passivation layers from the liquid environment which exists during use of the catheter, are placed on the flats, oriented to direct their respective laser beams distally, more-or-less parallel with local axis 8. The path of the light beam from laser chip 914a is illustrated as 400a in FIG. 9a. Thus, the light pulses are generated right at the distal end of the catheter, for use at the distal end of the catheter. The electrical drive for laser chip 914a is by way of an electrical path illustrated as 940a. Electrical path 940a may include either one or two conductors, for energizing any one or all of the laser chips 914a, 914b, and 914c. If electrical conduction path 940a has two conductors, the three laser diode chips 914a, 914b, and 914c may be energized or driven in parallel, in well-known fashion, by additional electrical conductors (not illustrated) extending between laser diode chips 914a, 914b, and 914c. If electrical conduction path 940 has a single electrical conductor, it must be paired with another conductor, illustrated in FIG. 9a as 940b, to provide a complete path for the flow of electrical current. As a further alternative, each (or some) of the laser diode chips may be energized by way of a separate or independent two-conductor path 940. FIG. 9a also illustrates that the body of the mass cap 18 may be made from a low-mass, high-strength dielectric composite material such as glass-reinforced epoxy, so long as the proximal end 18p of the mass cap 18 is coated with a titanium (or other suitable) metal layer 718.

FIG. 10 is a simplified representation of an optical fiber 1032 which may be used in a catheter according to the invention, together with a focussing device. In FIG. 10a, a distal portion of the optical fiber is designated 1032, and the focussing device is illustrated as a lens in the form of a cylindrical gradient-index lens 1010 bonded to the distal end of the optical fiber. The lens, which may be physically located within the resilient mounting of the body 12 of the catheter 11 (FIG. 1), focusses the light beam 1000 guided through the fiber as suggested by dash-lines 1002, to focus at point 1050*a* on the proximal surface of mass cap 1018. Naturally, other types of lenses may be used, or the distal end of the optical fiber 1032 may be polished with a curvature which tends to focus the beam.

The advantage of using a focussing device is to enhance local plasma generation to thereby enhance the generation of compression pulses or vibrations.

Figure 11A:
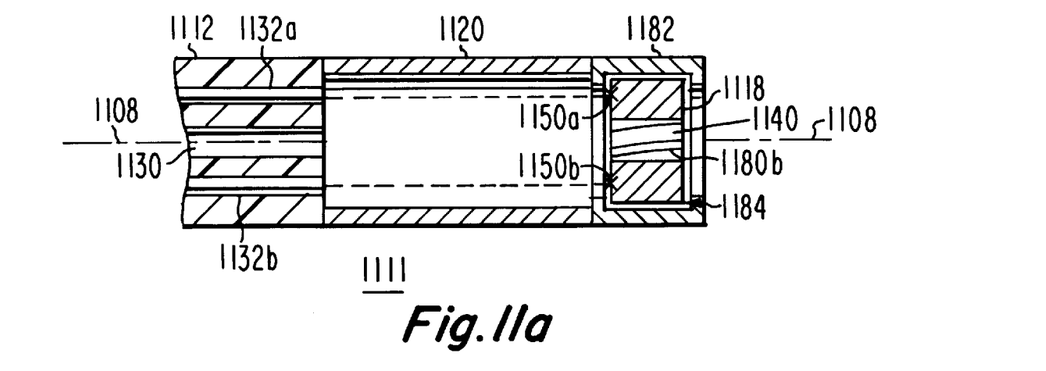
FIG. 11*a* is a simplified cross-sectional representation of another embodiment of a catheter according to an aspect of the invention, in which the mass cap rotates in response to the flow of fluid therethrough.
Figure 11B:
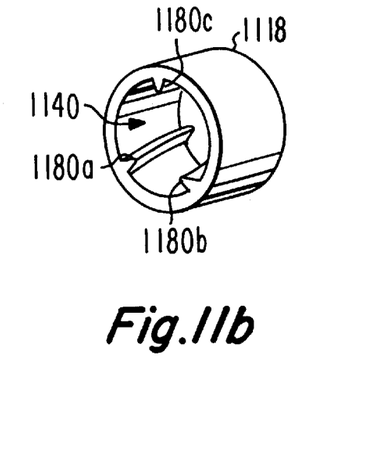
FIG. 11*b* is a simplified perspective or isometric view of the mass cap of FIG. 11*a*.
Figure 11C:
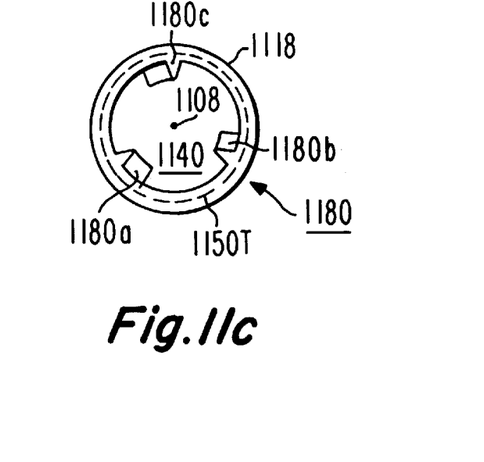
FIG. 11*c* is a simplified end view of the mass cap of FIG. 11*b*.

FIG. 11*a* is a simplified cross-sectional representation of another embodiment of a catheter according to an aspect of the invention, in which the mass cap rotates in response to the flow of fluid therethrough, FIG. 11*b* is a simplified perspective or isometric view of the mass cap of FIG. 11*a*, and FIG. 11*c* is a simplified end view of the mass cap of FIG. 11*b*. In FIG. 11*a*, the body of the catheter is designated 1112, and two of the optical paths are designated 1132*a* and 1132*b*. A central aspiration or medication infusion channel is designated 1130. A support arrangement for the mass cap is illustrated as a cylindrical structure 1120, and a mass cap bearing and support arrangement designated 1182 is connected to the distal end of support arrangement 1120. The mass cap bearing and support arrangement 1182 includes a peripheral channel designated as 1184, which retains mass cap 1118 against gross axial motion, and allows its rotation. As illustrated in more detail in FIGS. 11*b* and 11*c*, mass cap 1118 is in the form of a washer or disk with an axial aperture 1140. Axial aperture 1140 is fitted with a set 1180 of blades or impellers, which are illustrated as being three in number, and which are designated 1180*a*, 1180*b*, and 1180*c*. The blades or impellers are angled across the inner surface of aperture 1140 in a manner which is skewed relative to axis 1108. The skew of the impellers or blades of set 1180 is such as to generate a rotational moment when fluid flows through the aperture 1140. The direction of rotation of the mass cap 1118 will depend upon the direction of flow of the fluid. When an infusion pump or an aspiration pump 34*p* is connected to fitting 34 of FIG. 1, fluid pressure is generated which tends to move fluid through channel 1130 of catheter 1111 of FIG. 11*a*, which in turn causes a rotational moment to be imparted to the mass cap 1118 by the blades or impellers of set 1180. Since the mass cap is free to rotate within bearing or bushing 1184 of holder 1182 of FIG. 11*a*, the rotation takes place. If the infusion or medication pump, such as 34*p* of FIG. 1, is operated while laser pulses are applied through light paths 1132*a* and 1132*b* to locations 1150*a* and 1150*b* of FIG. 11*a*, the rotation of the mass cap will cause the locations of the impingement of the laser beams on the proximal surface of the mass cap, which are illustrated as 1150*a* and 1150*b* in the static representation of FIG. 11*a*, to be distributed along a track designated as 1150T in FIG. 11*c*. This distribution of the impingement locations along a track, in turn, reduces the wear or erosion which is experienced by any particular location along the track, resulting in less erosion at a given location for the same number of pulses, or some equivalent benefit. This, in turn, should allow a given catheter to be operated for a longer time interval before the mass cap is eroded through, or as a particularly advantageous benefit, it allows a thinner mass cap (or mass cap proximal surface coating) for a given duration of operation, which in turn translates into a less massive mass cap, and correspondingly a higher mechanical resonance frequency. The higher mechanical resonance frequency may be advantageous under some circumstances. In particular, erosion of the mass cap at the location(s) of impingement tends to change the light-source-to-target distance, which may lead to defocussing in those cases in which the beam is focussed on the mass cap. Defocussing, in turn, may lead to less efficient transduction between light energy and mechanical or acoustic energy.

Other embodiments of the invention will be apparent to those skilled in the art. For example, while the distal ends of the optical fibers, such as fiber 32*a* of FIG. 2*c*, have been illustrated as simply opening into the open region 42, their ends may be fitted with lenses or collimating arrangements, known in the art, for controlling the light. While the embodiment of FIG. 7 illustrates the covering of the entire proximal side of the mass cap with titanium, the titanium could be placed only at those locations, such as 50*a*, 50*b*, and 50*c* at which the laser beams impinge. While an illustrated and described embodiment of the invention uses the flow of fluid through the mass cap to rotate the mass cap, an electrical or other motor could be used instead. While a single spring 18 is illustrated, multiple interleaved springs may be used instead.

Thus, an ablation catheter system (10) according to the invention includes an ablation catheter 11, which includes an elongated, flexible body (12) defining a distal end (14), a proximal end (16), a local axis (8), and a mass cap (18) defining a proximal portion (18*p*) and a distal portion (18*d*). A resilient mounting arrangement (20) includes a proximal end (20*p*) and a distal end (20*d*). The proximal end (20*p*) of the resilient mounting arrangement (20) is physically coupled to the body (12) of the catheter (11), and the distal end (20*d*) of the resilient mounting arrangement (20) is physically coupled to the mass cap (18), for holding the mass cap (18) adjacent to the distal end (14) of the catheter body (12). The resilient mounting arrangment (20) is preferably coupled to the distal portion (18*d*) of the catheter body (12). The resilient mounting arrangement (20) defines at least (or one of) (a) transparent (832) and (b) physically open (42) regions, with the transparent (832) or open (42) regions lying between the distal end (14) of the catheter body (12) and the mass cap (18). The ablation catheter (11) also includes at least one laser light radiator or source (24: 414, 414*b*, 414*c*) for producing one or more light beam(s) (440*a*, 400*b*, 400*c*). The laser light source (24: 414, 414*b*, 414*c*) is located near the distal end (14) of the catheter body (12), and is oriented so as to project its light beam (440*a*, 400*b*, 400*c*) parallel to the local axis (8), through an open (42) or transparent (832) portion of the resilient mounting arrangement (20), to a proximal portion (18*p*) of the mass cap (18). The laser light beam (440*a*, 400*b*, 400*c*) may be focussed before impinging on the mass cap (18). The actual laser(s) which produces the light may be located outside of the body of the patient and external to the catheter itself, or made as part of the catheter and lie external to the body of the patient when in use, or they may be part of the catheter and located within the body of the patient when the catheter is in use.

In an advantageous embodiment, relative motion is generated between the mass cap (18) and the light beams (400), to thereby cause the location (50) of the impingement to move over the proximal surface (18*p*) of the mass cap (18) as a function of time.

In a particularly advantageous embodiment of the invention, the ablation catheter is part of an ablation 30 catheter system (10) in which the mass cap (18), in conjunction with the resilient mounting arrangement (20), makes a physically resonant system defining a fundamental resonant frequency. In this catheter system, a laser light source (FIG. 6) driving arrangement external to the catheter (12) drives the laser light source (414; 512) in such a manner as to generate the laser light in pulses having a repetition rate which is near the fundamental resonance frequency, or near a submultiple (subharmonic) of the fundamental resonance frequency, and for, together with the ablation catheter, forming an ablation catheter system.

In another embodiment of the catheter according to the invention, which may be used in the ablation catheter system, the laser light source(s) comprise semiconductor laser chips (914a, 914b, 914c), and further comprise an electrical conducting arrangement (940a, 940b) extending from the semiconductor laser chip(s) (914a, 914b, 914c) to the proximal end (14) of the catheter (11). Each of the laser light sources may include a laser (414, 414b, 414c) located outside the body of the catheter, a source of electrical energy (24p: 416) coupled to the laser (414, 414b, 414c) by an arrangement lying outside of the catheter body, and an optical fiber light path (32a, 32b, and 32c) extending from the laser (414, 414b, 414c), through the proximal end (16) of the catheter (11), through the body (12) of the catheter, and to the distal end (14) of the catheter.

In a particularly advantageous embodiment of the invention, the mass cap (18) further defines an aperture (40; 1140), and the body (12) of the catheter defines a lumen (30) extending from a region near the proximal end (16) of the catheter body (12) to the distal end (14) of the catheter, and the resilient mounting arrangement (20) also defines a path (42) extending from the aperture (40; 1140) of the mass cap (18) to the distal end of the lumen of the catheter body, for providing access for a guide wire, or for providing a path for aspiration of ablated material or for infusion. The aperture (40; 1140) of the mass cap (18), the path (42) of the resilient mounting arrangement (20), and that portion of the lumen (30) of the catheter body (12) near the distal end (14) of the catheter body (12) may be radially centered between the laser light sources (32ad: 914). The mass cap (18) and the body (12) of the catheter (11) may further define aspiration/infusion apertures, coupled together for the flow of fluid therebetween and together extending from a region near the proximal end of the catheter body to the distal end of the mass cap.

In another embodiment according to an aspect of the invention, the laser beam (440a, 400b, 400c) impinges upon different portions of the mass cap (18) at different times, so as to reduce the erosion of a particular area, and to distribute the erosion over a portion of the area of the mass cap (18), to thereby extend the useful life of the catheter arrangement. In a particular embodiment, this is accomplished by rotating the mass cap (18) in response to flow of fluid therethrough.

A more particular embodiment of the ablation catheter (11) according to the invention includes an elongated, flexible body (12) defining a distal end (14), a proximal end (16), and a local axis (8), and a mass cap (18) defining a proximal portion (18p) and a distal portion (18d). A resilient mounting arrangement (20) includes a proximal end (20p) and a distal end (20d). The proximal end (20p) of the resilient mounting arrangement (20) is physically coupled to the distal end (14) of the body (12) of the catheter, and the distal end (20d) of the resilient mounting arrangement (20) is physically coupled to the mass cap (18), for holding the mass cap (18) adjacent to the distal end (14) of the catheter body (12). The resilient mounting arrangement (20) defines at least one of a transparent region (832) and an open region (42) lying between the distal end (14) of the catheter body (12) and the mass cap (18). A plurality of laser light sources (32ad, 32bd, . . . : 914a, 914b, 914c) is provided, each of which produces a light beam (400a, 400b, 400c). Each of the laser light sources (32ad, 32bd . . . : 914a, 914b, 914c) is physically coupled to the distal end (14) of the catheter body (12). Each of the plurality of laser light sources (32ad, 32bd, . . . : 914a, 914b, 914c) is circumferentially located relative to the local axis (8), and equally spaced (120° in FIGS. 5 and 9b) about the local axis (8) relative to others of the laser light sources (32ad, 32bd, . . . : 914a, 914b, 914c), and oriented so as to project its light beam (400a, 400b, 400c) parallel to the local axis (8), through an optically transparent region (including an open region 42, 832) of the resilient mounting arrangement (20), to a proximal portion (18p) of the mass cap (18). In a particularly advantageous version of this embodiment, the mass cap (18)in conjunction with the resilient mounting arrangement (20) makes a physically resonant system defining a fundamental resonant frequency, and also includes a laser light source driving arrangement (24: 410, 412a, 412b, 412c). The laser light source driving arrangement (24: 410, 412a, 412b, 412c) includes an arrangement (410) for driving the laser light sources, so as to generate the laser light (400a, 400b, 400c) in pulses (310a, 310b, 310c) having a repetition rate which includes components near one of (or either of) (a) the fundamental frequency and (b) submultiples of the fundamental frequency. The laser light source driving arrangement (24) also, together with the ablation catheter (11), forms an ablation catheter system (10). The laser light sources (32ad, 32bd, . . .: 914a, 914b, 914c) at the distal end of the catheter body (12) may include semiconductor laser chips (914a, 914b, 914c), and may further include an electrical conducting arrangement (940a, 940b) extending from the semiconductor laser chips (914a, 914b, 914c) to the proximal end (18p) of the catheter (12). In another embodiment, each of the laser light sources (32ad, 32bd . . .: 914a, 914b, 914c) may include a laser (414. 414b. 414c) located outside the body (12) of the catheter (11), and an optical fiber light path (32a, 32b, 32c) extending from the external laser (414. 414b. 414c), through the proximal end (16) of the catheter (11), through the body (12) of the catheter (11), and to the distal end (14) of the catheter (11), and more particularly to the proximal end (18p) of the mass cap (18). In order to accommodate a guide wire, or for aspiration or infusion (aspiration/infusion), the mass cap (18; 1118) may further define an aperture (40; 1140), the body (12) of the catheter (11) may define a lumen (30) extending from a region near the proximal end (14) of the catheter body (12) to the distal end (14) of the catheter body (12), and the resilient mounting arrangement (20) may also define a path (42) extending from the aperture (40; 1140) of the mass cap (18; 1118) to the distal end (14) of the lumen (30) of the catheter body (18; 1118), and these paths (20, 40, 42) may be centered in the surrounding structure, if desired. If such a combination of lumens, open spaces, and apertures is provided for use with a guide wire, the mass cap of the catheter may also include a further aspiration/infusion aperture, and the body of the catheter may define a further aspiration/infusion lumen extending from a region near the proximal end of the catheter body to the distal end of the catheter body. In this last embodiment, the opening of the resilient arrangement may be used by both the guide wire and by the aspiration/infusion path.

What is claimed is:

1. An ablation apparatus including a catheter, said catheter comprising:

an elongated, flexible body defining a distal end, a proximal end, and a local axis;

a mass cap defining a proximal portion and a distal portion;

resilient mounting means including a proximal end and a distal end, said proximal end of said resilient mounting means being physically coupled to said distal end of said body of said catheter, and said distal end of said resilient mounting means being physically coupled to said mass cap, for holding said mass cap adjacent to said distal end of said body of said catheter, said resilient mounting means defining at least one of transparent and open regions lying between said distal end of said catheter body and said mass cap; said ablation apparatus further comprising at least one laser light source for producing a light beam, and located near said distal end of said catheter body, and oriented so as to project its light beam parallel to said local axis, through said resilient mounting means, to a proximal portion of said mass cap; wherein:

said mass cap in conjunction with said resilient mounting means makes a physically resonant system defining a fundamental resonant frequency; and further comprising:

a laser light source driving arrangement, said laser light source driving arrangement including means for driving said at least one laser light source, for generating said laser light in pulses having a repetition rate which is near one of (a) said fundamental frequency and (b) a subharmonic of said fundamental frequency, and for, together with said ablation catheter, forming an ablation catheter system.

2. A catheter according to claim 1, wherein said laser light source comprises at least one semiconductor laser chip, and further comprising electrical conducting means extending from said semiconductor laser chip to said proximal end of said body of said catheter.

3. A catheter according to claim 1, wherein said laser light source comprises:

a laser located outside said body of said catheter;

a source of electrical energy coupled to said laser by means lying outside of said catheter body; and an optical fiber light path extending from said laser through said proximal end of said body of said catheter, through said body of said catheter and to said distal end of said catheter body.

4. A catheter according to claim 1, wherein:

said mass cap further defines an aperture;

said body of said catheter defines a lumen extending from a region near said proximal end of said catheter body to said distal end of said catheter body; and said resilient mounting means also defines a light path extending from said aperture of said mass cap to the distal end of said lumen of said catheter body.

5. A catheter according to claim 4, wherein:

said laser light source comprises a plurality of locations adjacent said distal end of said catheter body at which laser light beams emanate parallel to said local axis; and said aperture of said mass cap, said path of said resilient mounting means, and that portion of said lumen of said catheter body near said distal end of said catheter body are radially centered between said plurality of locations at which said laser light beams emanate.

6. A catheter according to claim 4, wherein:

said mass cap defines a further aspiration/infusion aperture;

said body of said catheter defines a further aspiration/infusion lumen extending from a region near said proximal end of said catheter body to said distal end of said catheter body.

7. An ablation catheter according to claim 1, further comprising focussing means coupled to said light beam for focussing said light beam onto said proximal portion of said mass cap.

8. An ablation catheter according to claim 1, further comprising moving means for moving in a manner which results in relative motion of the point of impingement of said light beam on said mass cap over time.

9. An ablation catheter according to claim 8, wherein said moving means comprises means coupled to said mass cap for causing said mass cap to rotate.

10. An ablation catheter according to claim 9, wherein said moving means comprises a fluidic motor coupled to said mass cap.

11. An ablation catheter according to claim 10, wherein said fluidic motor includes an axial aperture extending through said mass cap, and impeller blades associated with said aperture, for causing a rotational moment on said mass cap in response to the flow of fluid through said aperture.

12. An ablation catheter, comprising:

an elongated, flexible body defining a distal end, a proximal end, and a local axis;

a mass cap defining a proximal portion and a distal portion;

a resilient mounting arrangement including a proximal end and a distal end, said proximal end of said resilient mounting arrangement being physically coupled to said distal end of said body of said catheter, and said distal end of said resilient mounting arrangement being physically coupled to said mass cap, for holding said mass cap adjacent to said distal end of said catheter body, said resilient mounting arrangement defining one of transparent and open regions lying between said distal end of said catheter body and said mass cap; and a plurality of laser light sources, each of which produces a light beam, each of said laser light sources being physically coupled to said distal end of said catheter body, each of said plurality of laser light sources being circumferentially located relative to said local axis, and equally spaced about said local axis relative to others of said laser light sources, so as to project its light beam parallel to said local axis, through a transparent region of said resilient mounting arrangement, to a proximal portion of said mass cap.

13. An ablation catheter system, comprising:

an elongated, flexible body defining a distal end, a proximal end, and a local axis;

a mass cap defining a proximal portion and a distal portion;

a resilient mounting arrangement including a proximal end and a distal end, said proximal end of said resilient mounting arrangement being physically coupled to said distal end of said body of said catheter, and said distal end of said resilient mounting arrangement being physically coupled to said mass cap, for holding said mass cap adjacent to said distal end of said catheter body, said resilient mounting arrangement defining one of transparent and open regions lying between said distal end of said catheter body and said mass cap; and a plurality of laser light sources, each of which produces a light beam, each of said laser light sources being physically coupled to said distal end of said catheter body, each of said plurality of laser light sources being circumferentially located relative to said local axis, and equally spaced about said local axis relative to others of said laser light sources, so as to project its light beam parallel to said local axis, through a transparent region of said resilient mounting arrangement, to a proximal portion of said mass cap; wherein:

said mass cap in conjunction with said resilient mounting arrangement makes a physically resonant system defining a fundamental resonant frequency; said ablation catheter system further comprising:

a laser light source driving arrangement, said laser light source driving arrangement including means for driving said laser light sources, for generating said laser light in pulses having a repetition rate which is near one of said fundamental frequency and harmonics of said fundamental frequency.

14. An ablation catheter system according to claim 13, wherein said laser light sources comprise semiconductor laser chips, and further comprise electrical conducting means extending from said semiconductor laser chips to said proximal end of said body of said catheter.

15. An ablation catheter system according to claim 13, wherein each of said laser light sources comprises:

a laser located outside said body of said catheter; and an optical fiber light path extending from said laser through said proximal end of said catheter, through said body of said catheter and to said distal end of said catheter body.

16. An ablation catheter system according to claim 13, wherein:

said mass cap further defines an aperture;

said body of said catheter defines a lumen extending from a region near said proximal end of said catheter body to said distal end of said catheter body; and said resilient mounting arrangement also defines a path extending from said aperture of said mass cap to said lumen at said distal end of said catheter body.

17. An ablation catheter system according to claim 16, wherein said aperture of said mass cap, said path of said resilient mounting arrangement, and that portion of said lumen of said catheter body near said distal end of said catheter body are radially centered between said laser light sources.

18. An ablation catheter system according to claim 16, wherein:

said mass cap further defines a further aspiration/infusion aperture;

said body of said catheter defines a further aspiration/infusion lumen extending from a region near said proximal end of said catheter body to said distal end of said catheter body.

19. An ablation catheter, comprising:

an elongated, flexible body defining a distal end, a proximal end, and a local axis, and also defining a lumen extending from a region near said proximal end of said catheter body to said distal end of said catheter body;

a mass cap defining a proximal portion and a distal portion, and also defining a central aperture extending from said proximal portion to said distal portion of said mass cap;

a resilient mounting arrangement including a proximal end and a distal end, said proximal end of said resilient mounting arrangement being physically coupled to said distal end of said body of said catheter, and said distal end of said resilient mounting arrangement being physically coupled to said mass cap, for holding said mass cap adjacent to said distal end of said catheter body with said central aperture coaxial with said local axis, said resilient mounting arrangement defining transparent regions lying between said distal end of said catheter body and said mass cap;

a plurality of laser light sources, each of which produces a light beam, each of said laser light sources being physically coupled to said distal end of said catheter body, each of said plurality of laser light sources being circumferentially located relative to said local axis, and equally spaced about said local axis relative to others of said laser light sources, so as to project its light beam parallel to said local axis, through a transparent region of said resilient mounting arrangement, to a proximal portion of said mass cap.

20. An ablation catheter according to claim 19, wherein said resilient mounting arrangement also defines an open path extending from said aperture at said proximal end of said mass cap to said lumen at said distal end of said catheter body.

21. An ablation catheter including an elongated, flexible body defining a distal end, a proximal end, and a local axis;

a mass cap defining a proximal portion of a particular material and a distal portion of a material other than said particular material;

a resilient mounting arrangement including a proximal end and a distal end, said proximal end of said resilient mounting arrangement being physically coupled to said body of said catheter, and said distal end of said resilient mounting arrangement being physically coupled to said mass cap, for holding said mass cap adjacent to said distal end of said catheter body, said resilient mounting arrangement defining at least one of transparent and open regions lying between said distal end of said catheter body and said mass cap; and a light source for producing a light beam, and located near said distal end of said catheter body, and oriented so as to project its light beam parallel to said local axis, through said resilient mounting arrangement, to a proximal portion of said mass cap.

22. An ablation catheter according to claim 21, wherein said particular material is titanium.

* * * * *